United States Patent
Kim et al.

(10) Patent No.: US 8,747,327 B2
(45) Date of Patent: Jun. 10, 2014

(54) APPARATUS AND METHOD FOR MEASURING BLOOD PRESSURE

(75) Inventors: Jong Pal Kim, Seoul (KR); Kun-soo Shin, Seongnam-si (KR); Sang-kon Bae, Seongnam-si (KR); Kyoung-ho Kang, Hwaseong-si (KR); Youn-ho Kim, Hwaseong-si (KR); Seok Chan Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 626 days.

(21) Appl. No.: 12/651,686

(22) Filed: Jan. 4, 2010

(65) Prior Publication Data

US 2010/0286538 A1  Nov. 11, 2010

(30) Foreign Application Priority Data

May 7, 2009  (KR) ........................ 10-2009-0039884

(51) Int. Cl.
*A61B 5/02* (2006.01)

(52) U.S. Cl.
USPC .......................................... 600/493; 600/503

(58) Field of Classification Search
USPC ........................... 600/481, 483–485, 490–503
See application file for complete search history.

(56) References Cited

U.S. PATENT DOCUMENTS

| 4,423,738 | A | | 1/1984 | Newgard | |
|---|---|---|---|---|---|
| 4,454,609 | A | * | 6/1984 | Kates | 381/320 |
| 4,830,017 | A | | 5/1989 | Perry et al. | |
| 4,924,871 | A | | 5/1990 | Honeyager | |
| 5,467,771 | A | * | 11/1995 | Narimatsu et al. | 600/485 |
| 5,651,370 | A | * | 7/1997 | Hersh et al. | 600/494 |
| 6,402,696 | B1 | * | 6/2002 | Nitzan et al. | 600/494 |
| 7,112,174 | B2 | * | 9/2006 | Satoh et al. | 600/500 |
| 7,306,563 | B2 | * | 12/2007 | Huang | 600/500 |
| 2003/0139674 | A1 | * | 7/2003 | Stergiopoulos et al. | 600/490 |
| 2005/0283087 | A1 | * | 12/2005 | Takazawa et al. | 600/500 |
| 2006/0195035 | A1 | * | 8/2006 | Sun | 600/503 |
| 2007/0225606 | A1 | * | 9/2007 | Naghavi et al. | 600/438 |

FOREIGN PATENT DOCUMENTS

| JP | 08-280638 A | 10/1996 |
|---|---|---|
| JP | 08-280639 A | 10/1996 |
| JP | 2001-008909 A | 1/2001 |
| JP | 2006-102184 A | 4/2006 |
| KR | 1020060091235 A | 8/2006 |
| KR | 1020070041944 A | 4/2007 |
| KR | 1020090001222 A | 1/2009 |

* cited by examiner

*Primary Examiner* — Michael Kahelin
*Assistant Examiner* — Yunqing Wang
(74) *Attorney, Agent, or Firm* — Cantor Colburn LLP

(57) ABSTRACT

A blood pressure measuring apparatus includes a sensing unit including a plurality of sensors sensing sphygmus waves at a measurement site, a selection unit selecting one sensor of the plurality of sensors based on the sphygmus waves sensed by the plurality of sensors, and a blood pressure estimation unit estimating blood pressure of the measurement site based on a sphygmus wave sensed by the selected sensor.

19 Claims, 12 Drawing Sheets

SENSOR (501)  FPCB (502)

SENSOR (511)  SEMICONDUCTOR CHIP (512)  FPCB (513)

APPARATUS AND METHOD FOR MEASURING BLOOD PRESSURE

CROSS-REFERENCE TO RELATED APPLICATIONS

This application claims priority to Korean Patent Application No. 10-2009-0039884, filed on May 7, 2009, and all the benefits accruing therefrom under 35 U.S.C. §119, the disclosure of which is incorporated herein in its entirety by reference.

BACKGROUND

1. Field

One or more embodiments of the invention relate to an apparatus and method for measuring blood pressure.

2. Description of the Related Art

Blood pressure is used as an index of a person's health condition. Apparatuses for measuring blood pressure are commonly used in medical institutions and at home. The United States Food and Drug Administration ("FDA") requires the standards for apparatuses for measuring blood pressure to comply with the requirements of the Association for the Advancement of Medical Instrumentation ("AAMI"). The American National Standards Institute ("ANSI")/AAMI SP10 issued by AAMI offers specification details, and safety and performance requirements for the apparatuses.

A systolic blood pressure is a pressure when an initial pulse sound is heard while an applied pressure is slowly reduced, after the pressure is applied to a site where arterial blood passes in order to stop the flow of blood. A diastolic blood pressure is a pressure when no pulse sound is heard. Digital hemadynamometers calculate blood pressure by detecting a waveform corresponding to a pressure measured while a pressure is applied to a blood vessel.

SUMMARY

One or more embodiments of the invention include an apparatus and method for analyzing sphygmus waves sensed at a measurement site by a plurality of sensors, in order to measure blood pressure. In addition, the one or more embodiments of the invention provide a computer readable recording medium storing instructions which control at least one computer processor to perform a method of measuring blood pressure.

One or more embodiments of the invention are not limited to the embodiments described above, and may also include other embodiments. These and other embodiments and features of the invention will become more fully apparent from the following description or may be learned by practice of the illustrated embodiments, as will be apparent to those of ordinary skill in the art.

According to one or more embodiments of the invention, a blood pressure measuring apparatus includes a sensing unit including a plurality of sensors sensing sphygmus waves at a measurement site, a selection unit selecting one sensor of the plurality of sensors based on the sphygmus waves sensed by the plurality of sensors, and a blood pressure estimation unit estimating blood pressure of the measurement site based on a sphygmus wave sensed by the selected sensor.

According to one or more embodiments of the invention, a blood pressure measuring method includes sensing sphygmus waves at a measurement site by using a plurality of sensors, selecting one sensor of the plurality of sensors based on sphygmus waves sensed by the plurality of sensors, and estimating blood pressure of the measurement site based on a sphygmus wave sensed by the selected sensor.

According to one or more embodiments of the invention, a computer readable recording medium stores instructions which control at least one computer processor to perform a method of measuring blood pressure. The method includes sensing sphygmus waves at a measurement site by using a plurality of sensors, selecting one sensor of the plurality of sensors based on sphygmus waves sensed by the plurality of sensors, and estimating blood pressure of the measurement site based on a sphygmus wave sensed by the selected sensor.

BRIEF DESCRIPTION OF THE DRAWINGS

These and/or other features will become apparent and more readily appreciated from the following description of the embodiments, taken in conjunction with the accompanying drawings of which.

DETAILED DESCRIPTION

Figure 1:
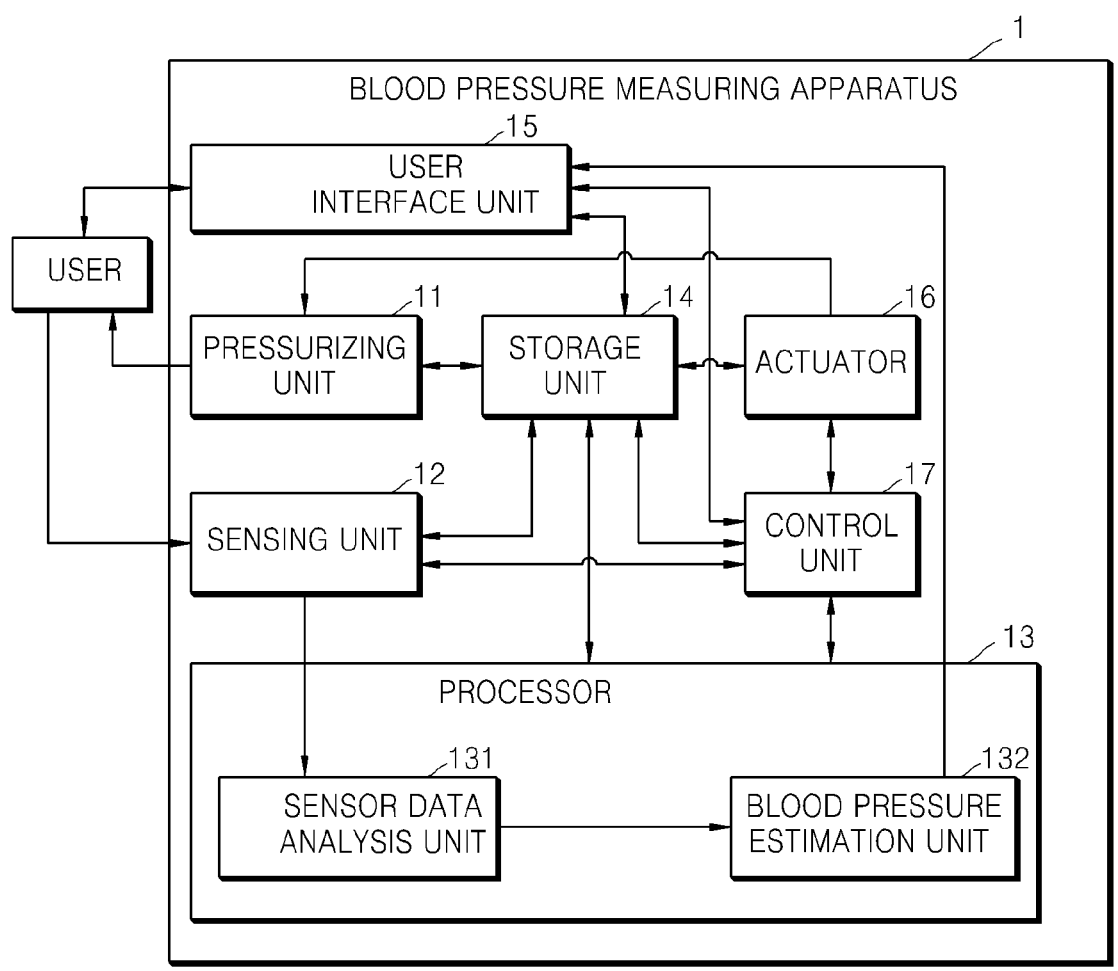
FIG. 1 is a schematic diagram illustrating an exemplary embodiment of a configuration of a blood pressure measuring apparatus, according to the invention.

Reference will now be made in detail to embodiments, examples of which are illustrated in the accompanying drawings, wherein like reference numerals refer to the like elements throughout. In this regard, the illustrated embodiments may have different forms and should not be construed as being limited to the descriptions set forth herein. Accordingly, the embodiments are merely described below, by referring to the figures, to explain features of the description.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "under" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "under" relative to other elements or features would then be oriented "above" relative to the other elements or features. Thus, the exemplary term "under" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

FIG. 1 is a diagram illustrating an exemplary embodiment of a configuration of a blood pressure measuring apparatus, according to the invention. Referring to FIG. 1, the blood pressure measuring apparatus 1 includes a pressurizing unit 11, a sensing unit 12, a processor 13, a storage unit 14, a user interface unit 15, an actuator 16, and a control unit 17. The pressurizing unit 11, the sensing unit 12, the processor 13, the storage unit 14, the user interface unit 15, the actuator 16 and/or the control unit 17 may form a part of or be included in a system, where the system may include a graphical user interface, external hardware devices, a computer processor, a computer network server or other similar signal processing equipment.

The processor 13 includes a sensor data analysis unit 131 and a blood pressure estimation unit 132. The processor 13 may be realized as an array of a plurality of logic gates, or in a combination of a general-use computer microprocessor and a memory storing a program to be executed in the general-use computer microprocessor. Alternatively, it will be understood by those of ordinary skill in the art that the processor 13 may be realized in various forms of hardware. In the specification, only hardware components that are related to embodiments will be described in order to prevent making the features of the embodiments vague. However, it will be understood by those of ordinary skill in the art that other general-use hardware components may be included, in addition to the hardware components illustrated in FIG. 1.

Referring to FIG. 1, the blood pressure measuring apparatus 1 according to the illustrated embodiment of the invention may include all instruments and apparatuses for measuring blood pressure, such as a blood pressure instrument, a blood pressure meter, a hemadynamometer, sphygmomanometer, etc.

The term blood pressure refers to pressure exerted on the walls of blood vessels by blood that is pumped out of the heart and flows in the blood vessels. In addition, blood pressure includes arterial blood pressure, capillary blood pressure, and venous blood pressure, according to the blood vessel where the blood pressure is measured. The arterial blood pressure varies according to the heartbeat. Also, blood pressure includes systolic blood pressure when blood flows into arteries as the ventricles of the heart contract, and diastolic blood pressure affecting the arterial wall due to the elasticity of the arterial wall, even when the ventricles expand and blood stays in the ventricles.

A sphygmus wave is a wave generated as a sphygmus is transmitted to peripheral arterioles. The term sphygmus refers to an artery repetitively expanding and relaxing due to the flow of blood in the artery whenever the heart beats. In other words, whenever the heart contracts, the blood is supplied to the entire body from the heart via the main artery, and thus pressure in the main artery changes. Such a change of pressure in the main artery is transmitted to peripheral arterioles of the hands and feet, and a sphygmus wave shows the change of pressure in the waveform. Sphygmus waves include both a direct current ("DC") component and an alternating current ("AC") component.

In general, blood pressure may be measured using a direct/indirect method, an invasive/noninvasive method, an intrusive/nonintrusive method, or the like. The direct method of measuring blood pressure involves directly inserting a catheter into, for example, the carotid arteries, and connecting the catheter to a manometer to measure blood pressure. The indirect method measures pressure when the bloodstream in a brachial artery or a radial artery is occluded by winding a blood-pressure cuff around a region to be measured, and then applying pressure to the region by injecting air into the blood-pressure cuff. The indirect method includes an entire pressurizing method using a cuff, or a regional pressurizing method of applying pressure to a portion of the blood vessel. The noninvasive method measures blood pressure from outside the blood vessels. The intrusive method uses a blood-pressure cuff to measure blood pressure, and the nonintrusive method measures blood pressure without using a blood-pressure cuff.

Examples of the noninvasive method include an auscultatory method, an oscillometric method, a tonometric method, and a method using a pulse transit time ("PTT").

The oscillometric method and the tonometric method are applicable to a digitized apparatus for measuring blood pressure. The oscillometric method measures the systolic pressure and the diastolic pressure by detecting a pulse wave generated in a depressurization process that depressurizes a body part at a constant speed. The detection of the pulse wave is conducted after sufficiently pressurizing the body part through which arterial blood flows so as to block arterial blood flow. This is similar to the Korotkoff sounds method. The oscillometric method may also be conducted in a pressurization process that pressurizes the body part at a constant speed. A pressure at which the amplitude of a pulse waveform is at a specific level may be measured as a function of the systolic pressure or the diastolic pressure, as compared with a pressure at which the amplitude of the pulse waveform is at a maximum. As used herein, the specific level means statistical characteristic ratios.

Alternatively, a pressure at which the amplitude of the pulse waveform varies greatly may be measured as a function of the systolic pressure or the diastolic pressure. During the depressurization process of the body part at a constant speed after the pressurization process, the systolic pressure is measured before the moment at which the amplitude of the pulse waveform is at the maximum, and the diastolic pressure is measured after the moment at which the amplitude of the pulse waveform is at the maximum. Conversely, in the pressurization process of the body part at a constant speed, the systolic pressure is measured after the moment at which the amplitude of the pulse waveform is at the maximum, and the diastolic pressure is measured before the moment at which the amplitude of the pulse waveform is at the maximum.

The statistical characteristic ratios are obtained by statistically analyzing sphygmus waves obtained by pressurizing body parts of subjects (e.g., humans or people), which are randomly selected. In other words, the pulse amplitude of the sphygmus wave is scaled for the maximum pulse amplitude to be 1, and the mean value of the pulse relative amplitude to the maximum pulse amplitude at the systolic and diastolic blood pressure of the subjects is calculated as the systolic and diastolic characteristic ratio, respectively.

An example of the oscillometric method includes a volume oscillometric method. The volume oscillometric method, which uses a cuff or an airbag as a pressurizing element, measures blood pressure based on a change in the amplitude of sphygmus waves measured while the internal air pressure of the pressurizing element is varied according to the amount of air being injected thereinto, and on the statistical characteristic ratios. In other words, when the amplitudes of the sphygmus waves reach the statistical characteristic ratios of systolic and diastolic pressure, the amplitudes of the sphygmus waves are estimated as systolic blood pressure and diastolic blood pressure based on the internal air pressure of the pressurized airbag, respectively.

According to the tonometric method, blood pressure can be measured continuously according to the magnitude and shape of the sphygmus wave that is generated when a predetermined pressure at which the blood flow in the artery is not completely blocked is applied to the body part.

Types of apparatus for measuring blood pressure include a wrist-type hemadynamometer and an arm-type hemadynamometer, according to body parts to which pressure is to be applied. Hereinafter, the blood pressure measuring apparatus 1 according to the illustrated embodiment will be described with reference to a wrist-type hemadynamometer where blood pressure is measured at a wrist, but it will be understood by those of ordinary skill in the art that the method described herein will be readily implemented in other types of hemadynamometers such as an arm-type, a finger-type, etc.

The pressurizing unit 11 pressurizes a wrist region of a subject. In the illustrated embodiment, the pressurizing unit 11 may include any pressurizing element, for example, a cuff, an airbag, etc., for applying pressure to a wrist region to be measured. The actuator 16 adjusts the pressurizing element, to be expanded or shrunk by driving the pressurizing unit 11. The pressurizing element may pressurize the entire wrist region or a portion of the wrist region, for example, under which the radial artery passes. Hereinafter, the pressurizing element will be described with reference to an embodiment of partially pressurizing a region under which the radial artery passes, but it will be understood by those of ordinary skill in the art that this disclosure is not limited to the embodiment.

Figure 2:
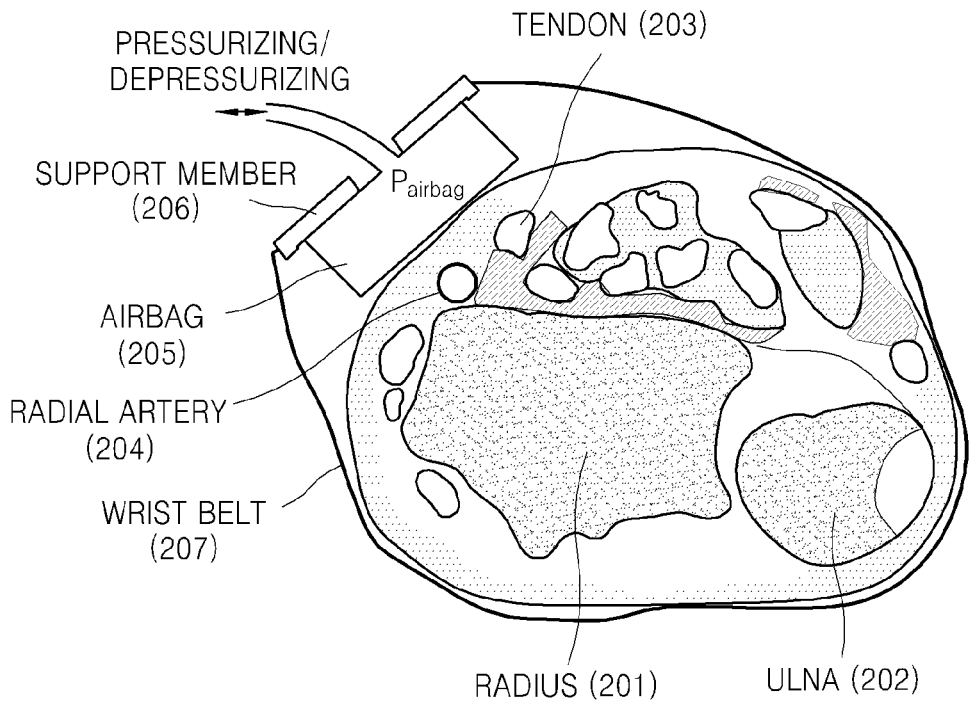
FIG. 2 is a cross-sectional view of an exemplary embodiment of a wrist region around which the blood pressure measuring apparatus of FIG. 1 is placed.

FIG. 2 is a cross-sectional view of an exemplary embodiment of a wrist region around which the blood pressure measuring apparatus 1 according to the illustrated embodiment of the invention is placed. FIG. 2 illustrates an exemplary embodiment of a method of partially pressurizing a portion of the wrist region. Referring to a cross-section of the wrist region in FIG. 2, a radius 201, an ulna 202, a tendon 203, and a radial artery 204, are illustrated. The blood pressure measuring apparatus 1 according to the illustrated embodiment measures the blood pressure of the radial artery 204 at a local skin surface region nearest to the radial artery 204. The local skin region nearest to the radial artery is least affected by other body parts (for example, the endodermis), when measuring the blood pressure of the radial artery 204.

Referring to FIG. 2, the regional pressurizing method involves pressurizing only a local skin surface under which the radial artery 204 passes, and not pressurizing the entire wrist region. An airbag 205 may be used as the pressurizing element. The airbag 205 adjusts the pressure acting on the local skin surface of the wrist under which the radial artery 204 passes, while being expanded or shrunk by the actuator 16. When the regional pressurizing method is used, the airbag 205, which is a pressurizing element attached to a solid support member 206, is fixed to the wrist such as by a wrist belt 207 attached to the solid member 206. Hereinafter, the regional pressurizing method will be described with reference to an exemplary embodiment of a method using the airbag 205 for pressurizing, but it will be understood by those of ordinary skill in the art that the wrist region may be partially pressurized by using other pressurizing elements apart from the airbag 205.

When the pressurizing unit 11 pressurizes a portion of the wrist region under which the radial artery 204 passes, such as by using the airbag 205 as the pressurizing element, the internal air pressure of the airbag 205 does not equal the pressure directly acting on the local skin surface. In addition, the internal air pressure of the airbag 205 may not be evenly distributed on the skin surface contacting the airbag 205 and may differ locally relative to various positions on the skin surface. The uneven distribution of the internal air pressure of the airbag 205 is due to the radius 201, the tendon 203 and the radial artery 204 being distributed under the skin surface of the wrist region and affecting the pressure acting on the skin surface. In other words, since the internal air pressure of the airbag 205, used in the regional pressurizing method, differs from actual pressure in the radial artery 204, systolic blood pressure and diastolic blood pressure estimated based on the internal air pressure of the airbag 205 have differences from the actual systolic blood pressure and diastolic blood pressure. Thus, when a change in the pressure at the skin surface under which the radial artery 204 passes while being pressurized is detected, blood pressure may be accurately measured.

Figure 3A:
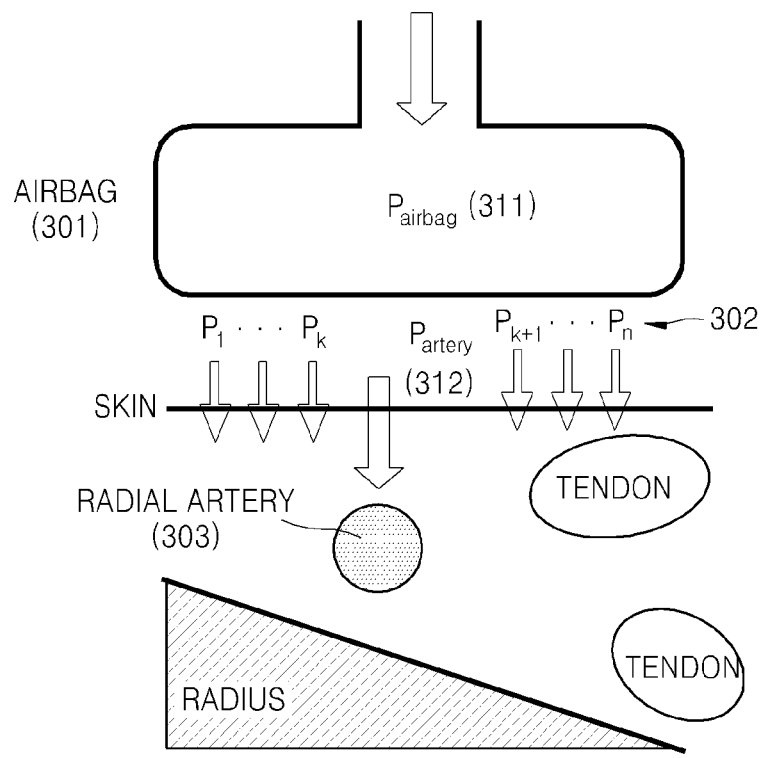
FIG. 3A illustrates an exemplary embodiment of the distribution of pressures on a skin surface locally pressurized by an airbag, according to the invention.

FIG. 3A illustrates an exemplary embodiment of a distribution of pressures on a skin surface locally pressurized by an airbag, according to an embodiment of the invention. Referring to FIG. 3A, as an internal air pressure $P_{airbag}$ of an airbag 301 increases, the skin surface of a wrist region is pressurized by the airbag 301. Since the radius, tendons, and the radial artery 303 are distributed under the skin surface of the wrist region, various pressures $P_1$ to $P_n$, which are denoted collectively by reference numeral 302, having different levels to that of the internal air pressure $P_{airbag}$ of the airbag 301, act locally on the skin surface. The local pressures $P_1$ to $P_n$ also have different levels compared to each other. Likewise, a pressure in the radial artery 303 has a different level than that of the internal air pressure $P_{airbag}$ of the airbag 301.

Figure 3B:
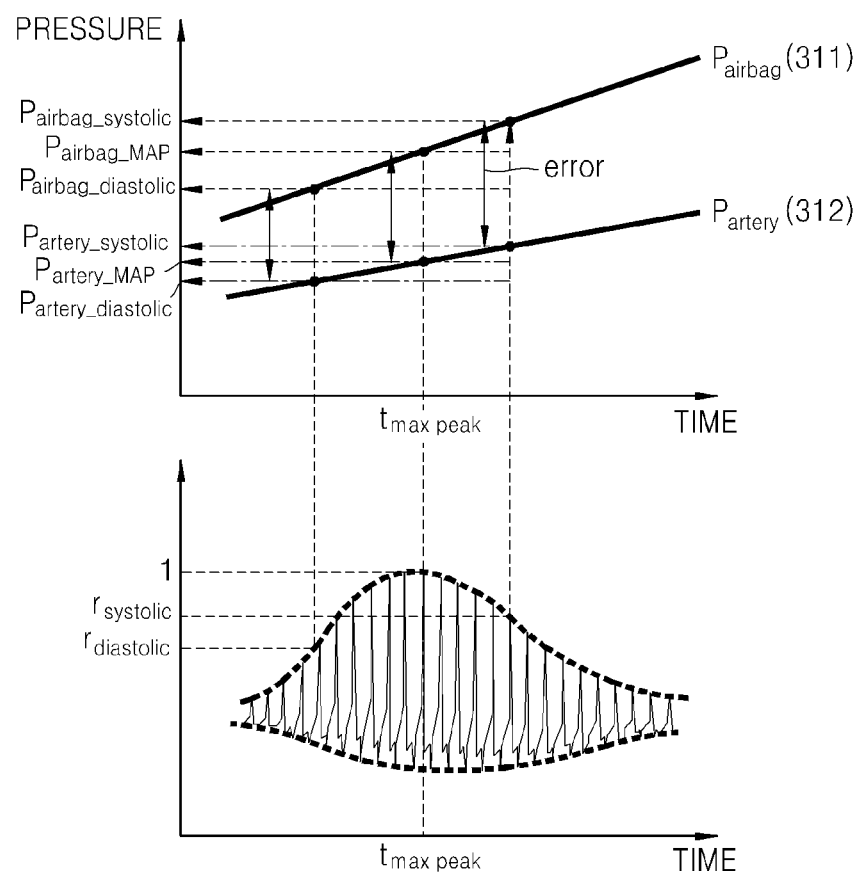
FIG. 3B illustrates errors in pressure occurring, based on local pressures acting on local skin surfaces having different levels from the internal air pressure of the airbag, as illustrated in FIG. 3A.

FIG. 3B illustrates that errors occur since the local pressures acting on the local skin surface, which are indicated by the arrows passing through the skin, have different levels from the internal air pressure $P_{airbag}$ of the airbag, as illustrated in FIG. 3A. Referring to FIG. 3B, when blood pressure is measured based on the internal air pressure $P_{airbag}$, which is denoted by reference numeral 311, of the airbag 301 using the volume oscillometic method, systolic blood pressure and diastolic blood pressure may be measured based on the sphygmus waves that are sensed while the measurement site is pressurized (e.g., indicated by the arrow pointing into the airbag 301) by the internal air pressure $P_{airbag}$ of the airbag 301, which constantly increases, and on the statistical characteristic ratios. In other words, the internal air pressures at points of time where the sphygmus wave has an amplitude corresponding to a ratio $r_{systolic}$ and an amplitude corresponding to a ratio $r_{diastolic}$, respectively, with respect to the maximum amplitude at a point of time $t_{max\_peak}$ at which the sphygmus wave has the maximum amplitude, are determined as the systolic blood pressure $P_{airbag\_systolic}$ and the diastolic blood pressure $P_{airbag\_diastolic}$, respectively, measured based on the internal air pressure of the airbag 301.

However, the actual pressure $P_{artery}$, denoted by reference numeral 312, in the radial artery is different from the internal air pressure $P_{airbag}$, denoted by reference numeral 311, of the airbag 301. In other words, the internal air pressure $P_{airbag}$ 311 of the airbag increases at the same rate, whereas the actual pressure $P_{artery}$ 312 in the radial artery is smaller than the internal air pressure $P_{airbag}$ 311 of the airbag. Thus, the actual systolic blood pressure $P_{artery\_systolic}$ and diastolic blood pressure $P_{artery\_diastolic}$ of the radial artery 303 measured based on the actual pressure $P_{artery\_MAP}$ and the statistical characteristic ratios $r_{systolic}$ and $r_{diastolic}$ are different from the systolic blood pressure $P_{airbag\_systolic}$ and the diastolic blood pressure $P_{airbag\_diastolic}$, respectively, measured based on the internal air pressure $P_{airbag\_MAP}$ of the airbag 301. In other words, the volume oscillometric method of measuring blood pressure based on the internal air pressure of the airbag may be inaccurate. Thus, when blood pressure is measured by using the volume oscillometric method based on the actual pressure in the radial artery, blood pressure may be more accurately measured. Hereinafter, an exemplary embodiment of more accurately measuring blood pressure based on the actual pressure in the radial artery will be described.

Referring back to FIG. 1, the sensing unit 12 includes a plurality of sensors, wherein each of the sensors senses sphygmus waves at a wrist region that is a measurement site. The sensing unit 12 is attached to a pressurizing element, such as an airbag, and is brought in contact with the local skin surface of the wrist region to sense sphygmus waves. The sensing unit 12 transmits the sensed sphygmus waves to a selection unit (not shown) in the sensor data analysis unit 131.

The sensors in the sensing unit 12 are pressure sensors sensing a change in pressure. Most pressure sensors convert a sensed change in pressure into an electrical signal. Herein, a change in pressure sensed at the wrist region corresponds to a sphygmus wave, which includes both a direct current ("DC") component and an alternating current ("AC") component. Thus, pressure sensors that are able to sense both the DC and AC components are used.

Types of pressure sensors include, but are not limited to, a piezoresistive pressure sensor, a capacitive pressure sensor, etc. In an exemplary embodiment, the piezoresistive pressure sensor senses pressure by using a piezoresistive element, of which a resistance varies according to an external pressure applied thereto. The capacitive pressure sensor senses pressure by converting a change in capacitance, which occurs as the space between opposing electrode plates is varied by an external pressure, into an electrical signal. However, the pressure sensor used in the illustrated embodiment may include, without limitation, any pressure sensor capable of sensing both AC and DC components from a change in pressure.

Each of the sensors of the sensing unit 12 may have a sensing width in order to sense a sphygmus wave within the sensing width at a local skin surface. Herein, the sensing width is parallel to the direction of traverse of the radial artery underlying the local skin surface of the wrist region, and is equal to or smaller than a statistical diameter of the radial artery. The sensing width is for accurately sensing just the sphygmus wave at the local skin surface nearest to the radial artery. In one exemplary embodiment, if a statistical diameter of the radial artery is about 2 millimeters (mm), the sensing width of each sensor may be equal to or smaller than about 2 mm. However, it will be understood by those of ordinary skill in the art that the sensing width is not limited, and may be greater than a statistical diameter of the radial artery, and/or may be determined based on the diameter of any artery of other parts of the body, and not just based on the radial artery of the wrist.

Figure 4A:
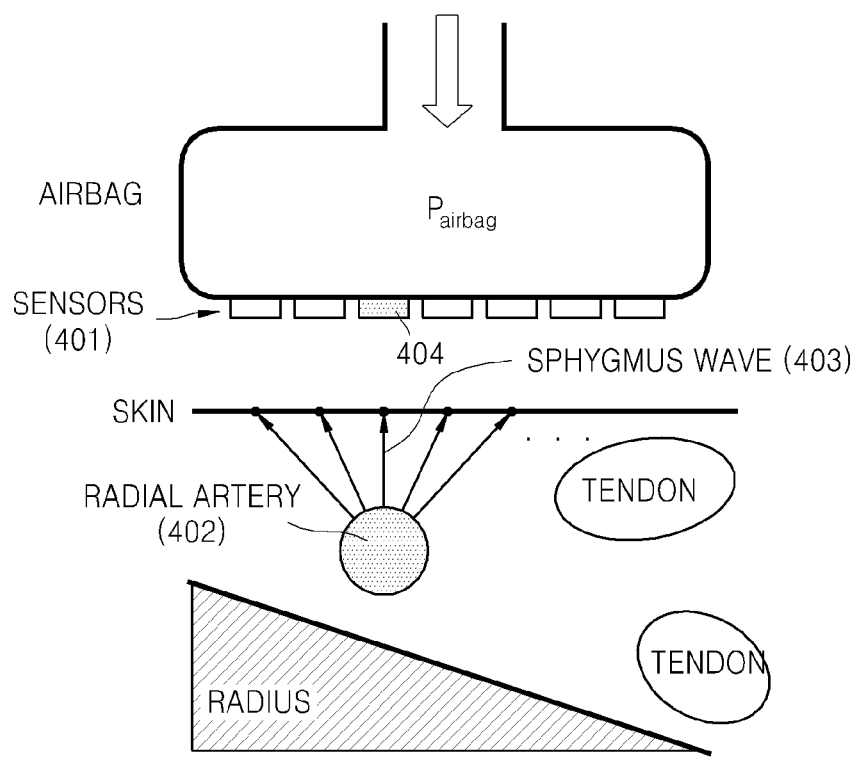
FIG. 4A illustrates an exemplary embodiment of detecting sphygmus waves at a local skin surface by using a plurality of sensors attached to a bottom of a pressurizing element, according to the invention.

FIG. 4A illustrates an exemplary embodiment of detecting sphygmus waves at a local skin surface, by using a plurality of sensors attached to a bottom of the pressurizing element which faces the local skin surface, according to an embodiment of the invention. Referring to FIG. 4A, a plurality of sensors 401 are attached to the bottom of an airbag used as the pressurizing element. The plurality of sensors 401 correspond to a sensor array to be described below. Each of the sensors is a pressure sensor and senses sphygmus waves at a local skin surface, while being pressed into contact against the local skin surface by the airbag.

Each of the sensors may have a sensing width that is equal to or smaller than the diameter of the radial artery 402. The sphygmus waves sensed by the plurality of sensors 401 may include a sphygmus wave 403 sensed at a local skin surface nearest to the radial artery 402, and sphygmus waves sensed at other local skin surfaces at a distance away from the radial artery 402. Thus, if blood pressure is measured based on the sphygmus wave 403 sensed by an individual discrete sensor 404 from among the plurality of sensors 401 as being nearest to the radial artery 402, blood pressure may be accurately measured with a smaller error with respect to actual blood pressure. The sensor 404 being nearest to the radial artery 402 is shown with a same pattern as the radial artery 402 in FIG. 4A. Those sensors 404 that are disposed at a distance away from the radial artery 402, are shown with no pattern (e.g., white).

Figure 4B:
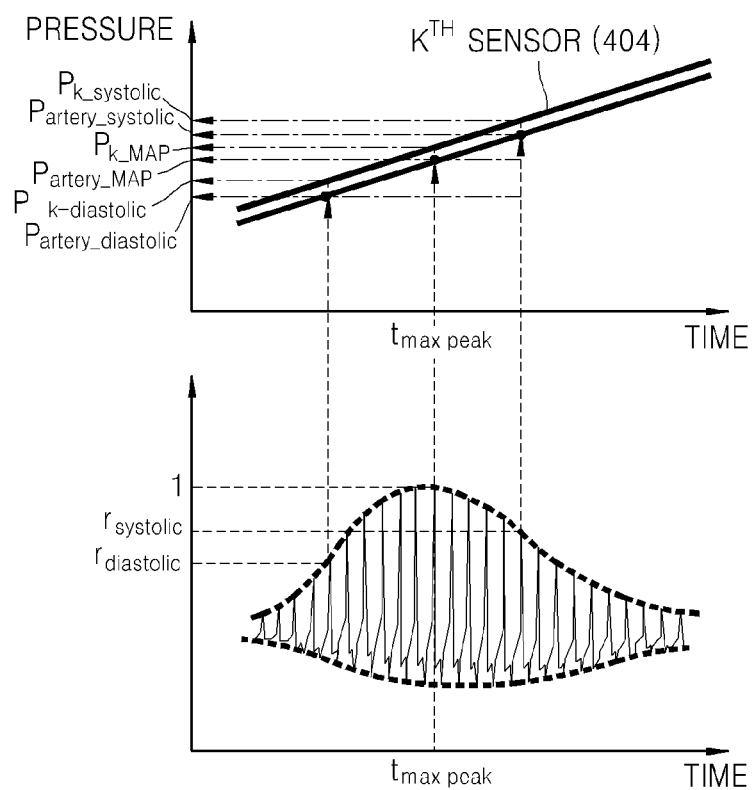
FIG. 4B illustrates an error with respect to actual blood pressure is reduced by using the plurality of sensors illustrated in FIG. 4A.

FIG. 4B illustrates that an error with respect to actual blood pressure is reduced by using the plurality of sensors illustrated in FIG. 4A. Referring to FIG. 4B, when systolic blood pressure $P_{k\_systolic}$ and diastolic blood pressure $P_{k\_diastolic}$ are measured using the sphygmus wave sensed by the sensor 404 (see FIG. 4A), which contacts the local skin surface nearest to the radial artery 402, the systolic blood pressure $P_{k\_systolic}$ and the diastolic blood pressure $P_{k\_diastolic}$ are closer to and have smaller errors with respect to the actual systolic blood pressure $P_{artery\_systolic}$ and diastolic blood pressure $P_{artery\_diastolic}$ of the radial artery 402. In comparison, FIG. 3B illustrates a larger error for a less accurate volume oscillometric method of measuring blood pressure based on the internal air pressure of the airbag where sensors are not used.

The structure of the sensing unit 12 will now be described in detail. The sensing unit 12 is a sensor array consisting of a plurality of sensors. The plurality of sensors in the sensor array, which constitutes the sensing unit 12, are arranged in a first direction to traverse the radial artery (e.g., be substantially perpendicular to the longitudinal extension of the radial artery). Since the plurality of sensors is arranged as described above, at least one of the plurality of sensors may accurately sense a sphygmus wave at the local skin surface nearest to the radial artery, even when a user arbitrarily wears the blood pressure measuring apparatus 1 on his/her wrist.

In an exemplary embodiment, the sensing unit 12 is a sensor array in which a plurality of rigid substrates are arrayed, and each rigid substrate is configured to have a relative movement with respect to neighboring rigid substrates. Each of the rigid substrates include at least two sensors disposed thereon. The sensor array of the sensing unit 12 as described herein may be implemented in various forms, for example, an array structure of sensors, or a printed circuit board ("PCB") on which a plurality of sensors are packaged. Hereinafter, exemplary embodiments of the sensor array of the sensing unit 12 will be described in detail.

The sensing unit 12 may include a sensor array formed by packaging a plurality of semiconductor chips each including a number of sensors packed therein, on a flexible printed circuit board ("FPCB").

In particular, a semiconductor chip for the sensing unit 12 may be formed by packaging a number of sensors on a solid substrate, such as a silicon wafer. Herein, the semiconductor chip may be a chip packaged from a plurality of silicon pressure sensors or microelectromechanical system ("MEMS") pressure sensors. Exemplary embodiments of the semiconductor chip may include, but are not limited to, a semiconductor chip packaged exclusively from pressure sensors for sensing pressure, a system-on-chip ("SoC") including various functional chips on a single chip to systematically perform various functions in the single chip, etc. The sensors packaged on the semiconductor chip have a sensing width, as described above.

As used herein, a printed circuit board ("PCB") refers to a substrate with a circuit, just before electronic parts are mounted thereon, the circuit being formed of a conductive material, such as a copper (Cu) foil, on an electrically insulating substrate. As electronic devices have become smaller, a FPCB has been developed for mobile phones, cameras, etc. In general, the FPCB refers to a substrate that may be bent like a flexible plastic film or a metal thin film.

The reason for forming the structure of the senor array with a plurality of sensors as described above lies in the fact that the skin surface of the wrist at which sphygmus waves are to be sensed is not flat, but rather is curved. Thus, every sensor may not contact the skin surface nor sense a sphygmus wave if the plurality of sensors are formed on a single, inflexible solid substrate. Thus, a plurality of semiconductor chips each including a number of sensors may be packaged on a single unitary and indivisible FPCB, so that sphygmus waves may be sensed in units of the number of sensors in each semiconductor chip in contact with the skin surface.

According to another exemplary embodiment, the sensing unit 12 may include a sensor array formed by packaging a plurality of sensors on a single unitary and indivisible FPCB. In addition, each of the sensors has a sensing width, as described above. Unlike the former embodiment in which the plurality of semiconductor chips each including a number of sensors are packaged on the FPCB, a number of sensors are directly packaged on a FPCB, without the semiconductor chips, in the illustrated embodiment. In the illustrated embodiment, due to the flexibility of the FPCB, each of the sensors packaged on the FPCB may directly contact the skin surface and sense sphygmus waves, irrespective of whether the skin surface is curved or moves.

It will be understood by those of ordinary skill in the art that the structure of the sensor array of the sensing unit 12 is not limited to the exemplary embodiments described above, and may be varied according to a usage environment of a user.

Figure 5A:
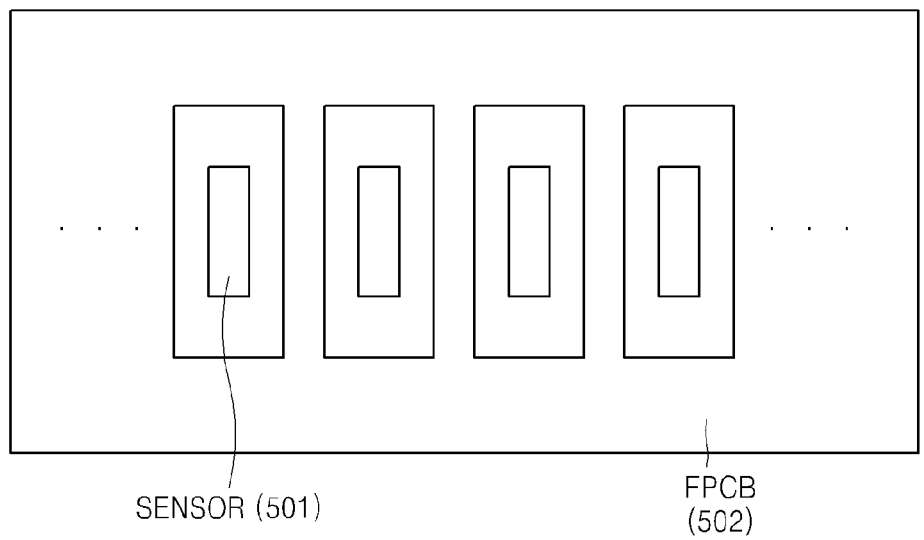
FIG. 5A illustrates an exemplary embodiment of a structure of a sensor array of a sensor unit, according to the invention.

FIG. 5A illustrates a structure of an exemplary embodiment of a sensor array of the sensor unit 12, according to the invention. Referring to FIG. 5A, the sensor array has a structure in which a plurality of sensors 501 are packaged on a FPCB 502. Since the plurality of sensors 501 are individually attached to the FPCB 502, and the FPCB 502 is configured to be bent, each of the individual sensors 501 may contact the skin surface of the wrist to sense sphygmus waves.

Figure 5B:
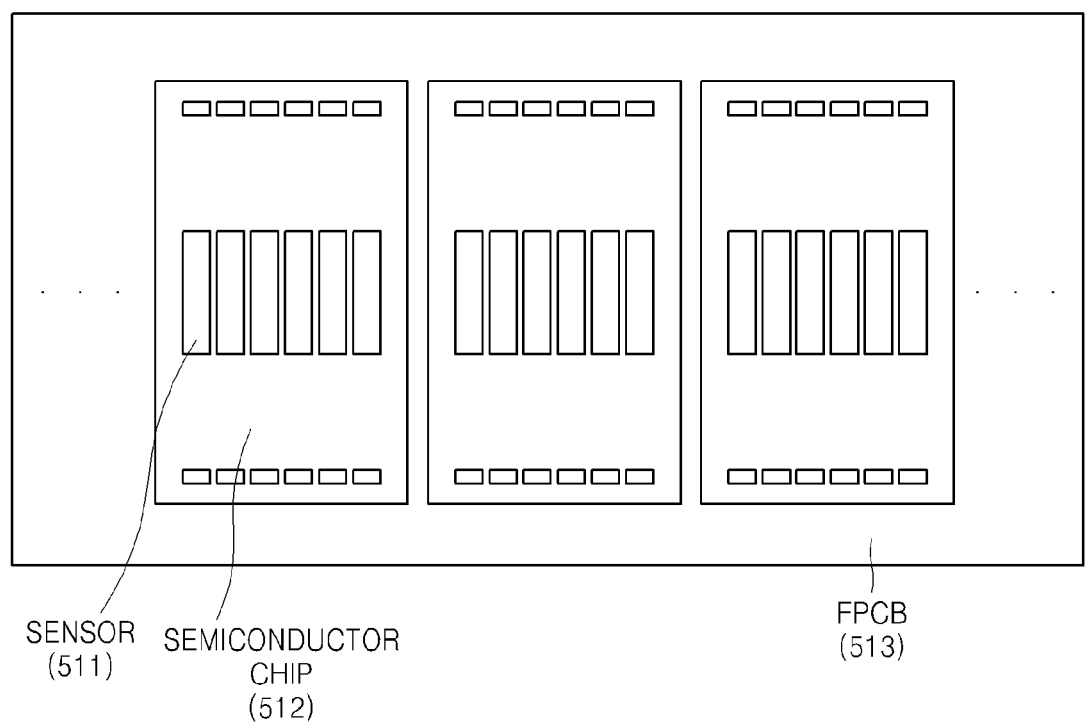
FIG. 5B illustrates another exemplary embodiment of a structure of a sensor array of the sensor unit, according to the invention.

FIG. 5B illustrates another exemplary embodiment of a structure of a sensor array of the sensor unit 12, according to the invention. Referring to FIG. 5B, the sensor array has a structure in which a plurality of semiconductor chips 512 are packaged on a single unitary indivisible FPCB 513. Each of an individual semiconductor chip 512 includes a number of discrete sensors 511 packaged on a solid substrate, such as a silicon wafer. If the plurality of sensors 511 are arranged directly on the FPCB 513, a larger sensing dead zone may result between the sensors 511. In order to reduce such an invalid sensing dead zone between adjacent sensors 511, an appropriate number of sensors 511 may be directly integrated onto a semiconductor chip 512. Then, a plurality of such semiconductor chips 512 having an appropriate size, each including the appropriate number of sensors 511, may be mounted on the FPCB 513 in order to offer flexibility.

As described above, each of the sensors 501 senses sphygmus waves within a sensing width. The sensing unit 12 in FIG. 5A and FIG. 5B transmits electrical signals associated with the sphygmus waves sensed by the sensors 501 and 511 to a selection unit (not shown) of the sensor data analysis unit 131 via the FPCB 502 and 513.

Referring back to FIG. 1, the processor 13 includes the sensor data analysis unit 131 and the blood pressure estimation unit 132. The sensor data analysis unit 131 analyzes the sphygmus waves sensed by the plurality of sensors, based on the waveform characteristics of the sphygmus waves after being filtered in order to select one of the sensors, and transmits information on the sphygmus wave sensed by the selected sensor to the blood pressure estimation unit 132.

Figure 6:
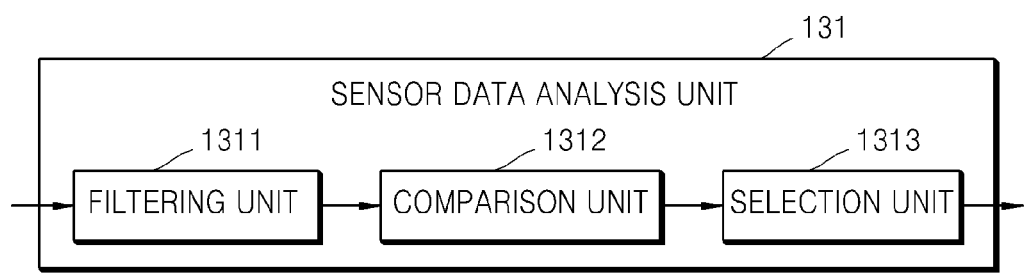
FIG. 6 is a detailed schematic diagram of an exemplary embodiment of a sensor data analysis unit illustrated in FIG. 1.

FIG. 6 is a detailed diagram of an exemplary embodiment of the sensor data analysis unit 131 illustrated in FIG. 1. Referring to FIG. 6, the sensor data analysis unit 131 includes a filtering unit 1311, a comparison unit 1312, and a selection unit 1313.

The filtering unit 1311 filters the sphygmus waves sensed by the plurality of sensors by allowing a high-frequency component and a low-frequency component of the sphygmus waves to pass. The filtering unit 1311 transmits the passed sphygmus waves to the comparison unit 1312. The filtering unit 1311, the comparison unit 1312 and the selection unit 1313 may form a part of or be included in a system, where the system may include a graphical user interface, external hardware devices, a computer processor, a computer network server or other similar signal processing equipment.

In particular, the filtering unit 1311 passes the sphygmus waves through a high-pass filter ("HPF") and a low-pass filter ("LPF"). In other words, a sphygmus wave sensed by one sensor passes through both the HPF and LPF, thereby being filtered according to its frequency band, and sphygmus waves sensed by the other sensors pass through both the HPF and LPF, thereby being filtered according to their frequency band.

The HPF selectively passes high-frequency signals having a higher frequency than a cutoff frequency and attenuates low-frequency signals in order to filter sphygmus waves only having a high-frequency component. The LPF selectively passes low-frequency signals of the sphygmus waves having a lower frequency than the cutoff frequency in order to filter sphygmus waves only having a low-frequency component. The HPF and the LPF are understood by those of ordinary skill in the art, and thus a detailed description thereof will not be provided herein.

Figure 7:
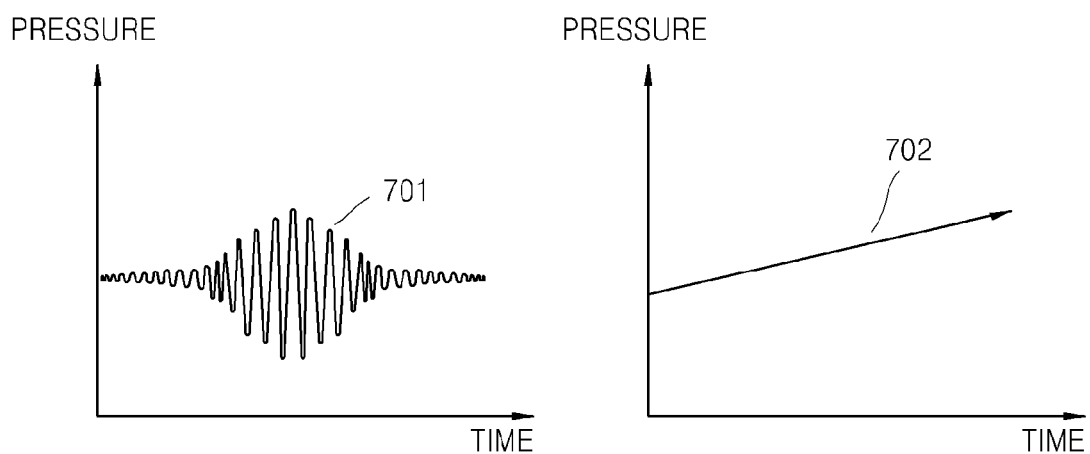
FIG. 7 illustrates graphs of an exemplary embodiment of a sphygmus wave passed through a high-pass filter ("HPF") and a low-pass filter ("LPF") of a filtering unit, respectively, after being sensed by one sensor of the sensing unit, according to the invention.

FIG. 7 illustrates graphs of an exemplary embodiment of a sphygmus wave passed through the HPF and the LPF of the filtering unit 1311, respectively, after being sensed by one sensor of the sensing unit 12, according to the invention.

Referring to FIG. 7, a sphygmus wave 701 passed through the HPF and a sphygmus wave 702 passed through the LPF are plotted as graphs of pressure with respect to time. With respect to the sphygmus wave 701 passed through the HPF, the amplitude of the sphygmus wave gradually increases to a maximum level and then decreases. The high frequency sphygmus wave gradually increases to a maximum level and then decreases because the sphygmus wave is sensed while the wrist region is increasingly pressurized using the pressurizing element. The statistical characteristic ratios described above are represented as ratios of sphygmus wave amplitude at systolic blood pressure and diastolic blood pressure with respect to the maximum amplitude of the sphygmus wave that is normalized to "1". Next, with respect to the sphygmus wave 702 passed through the LPF, the low-frequency sphygmus wave 702 increases at a constant rate with time. The low-frequency sphygmus wave 702 increases at a constant rate because the local skin surface is consistently pressurized by a sensor of the sensing unit 12.

The comparison unit 1312 compares the waveform characteristics of the sphygmus waves filtered by the HPF of the filtering unit 1311, and compares the waveform characteristics of the sphygmus waves filtered by the LPF of the filtering unit 1311. The results of comparison by the comparison unit 1312 are transmitted to the selection unit 1313.

In particular, the comparison unit 1312 compares the maximum amplitudes of the sphygmus waves, which are sensed by the plurality of sensors, filtered through the HPF. In addition, the comparison unit 1312 compares slope characteristics of the sphygmus waves filtered through the LPF. The comparison unit 1312 may also compare widths of the sphygmus waves filtered through the HPF of the filtering unit 1311.

The local skin surface nearest to the radial artery is least affected by the internal tissues of the wrist (for example, by the thickness of the endodermis), than other local skin surfaces. Thus, a sphygmus wave sensed at the local skin surface nearest to the radial artery has a larger intensity than the sphygmus waves sensed at the other local surfaces. Thus, the maximum amplitude of the sphygmus wave, which is sensed at the local skin surface nearest to the radial artery and filtered through the HPF, is larger than the maximum amplitudes of the sphygmus waves which are sensed at the other local skin surfaces and filtered through the HPF. In addition, since the skin local surface nearest to the radial artery is less affected by the internal tissue of the wrist than other local skin surfaces, the applied pressure is most effectively transmitted to the radial artery through the skin local surface nearest to the radial artery. Thus, the pressure in the radial artery may be reflected on the sphygmus wave sensed at the local skin surface nearest to the radial artery and having the larger intensity, rather than on the sphygmus waves sensed at the other local surfaces away from the radial artery, having relatively lower intensities.

The selection unit 1313 selects one of the plurality of sensors of the sensing unit 12 based on the results of comparison by the comparison unit 1312. In other words, the selection unit 1313 selects one of the sensors by analyzing which of the sphygmus waves filtered through the HPF has the maximum amplitude, by analyzing the slope characteristics of the sphygmus waves filtered through the LPF, or by analyzing the widths of the sphygmus waves filtered through the HPF of the filtering unit 1311. The selection unit 1313 transmits information on the sphygmus wave sensed by the selected sensor to the blood pressure estimation unit 132 (FIG. 1).

Figure 8A:
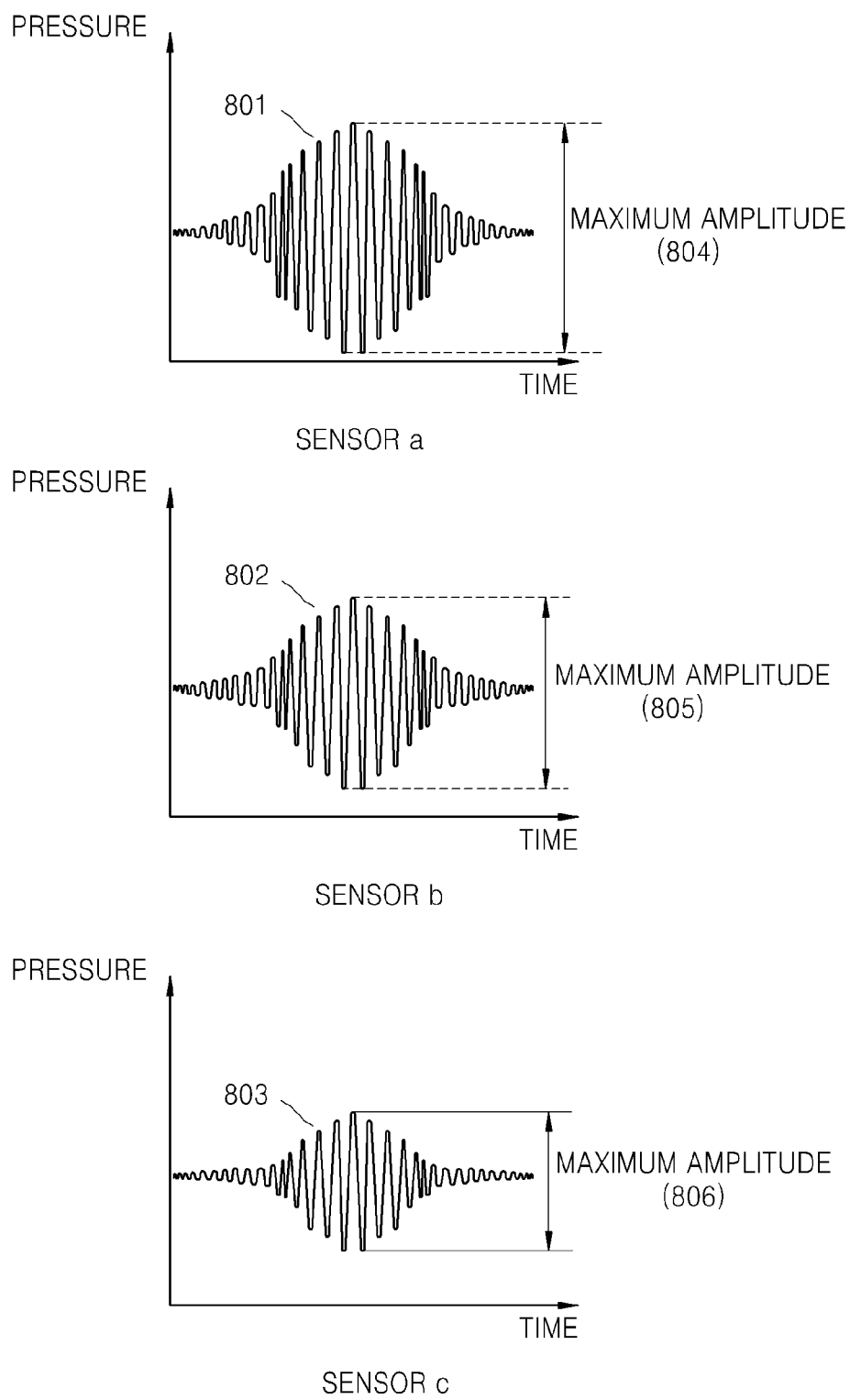
FIG. 8A illustrates an exemplary embodiment of the results of high-pass filtering sphygmus waves sensed by the plurality of sensors in the filtering unit of FIG. 6, according to the invention.

FIG. 8A illustrates an exemplary embodiment of the results of high-pass filtering the sphygmus waves sensed by the plurality of sensors, in the filtering unit 1311, according to the invention. Referring to FIG. 8A, sensor a, sensor b and sensor c are selected from among the plurality of sensors of the sensing unit 12. Sensor a senses a sphygmus wave at the local skin surface nearest to the radial artery, and sensor b and sensor c sense sphygmus waves at other local skin surfaces. According to the results of filtering the sphygmus waves sensed by the sensors a, b, and c through the HPF, the maximum amplitude 804 of the sphygmus wave sensed by sensor a is greater than the maximum amplitudes 805 and 806 of the respective sphygmus waves sensed by the sensors b and c. In other words, the sensor sensing a sphygmus wave at the local skin surface nearest to the radial artery may be selected by comparing the maximum amplitudes of the sphygmus waves filtered through the HPF.

Figure 8B:
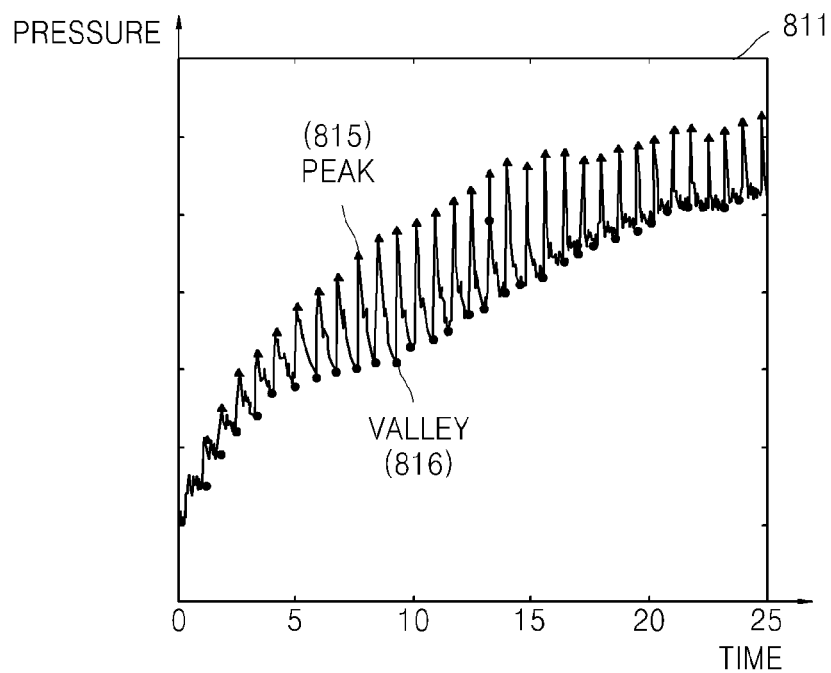
FIGS. 8B and 8D illustrate exemplary embodiments of sphygmus waves sensed respectively by different sensors of the sensing unit, according to the invention.
Figure 8C:
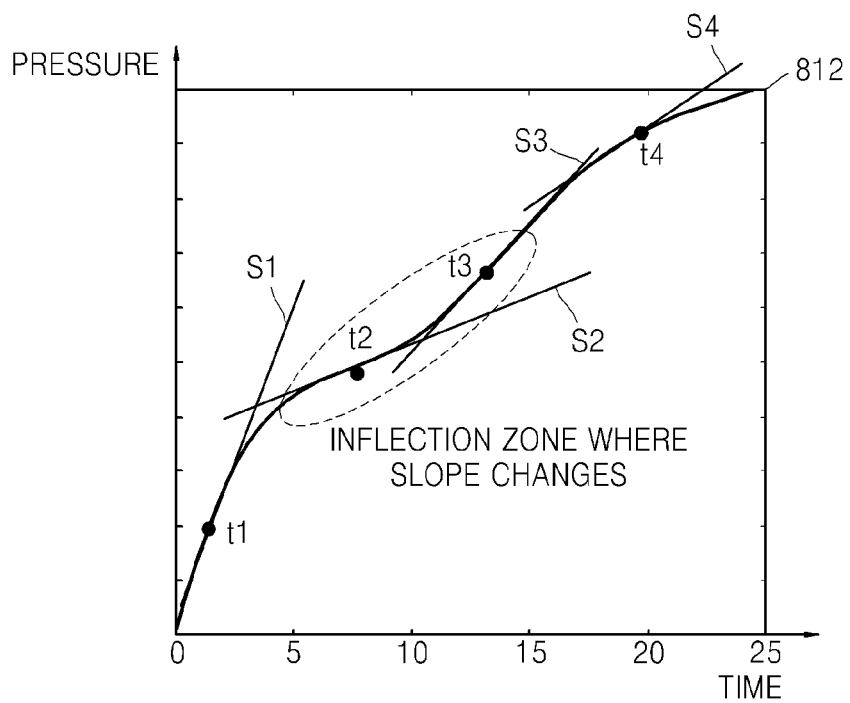
FIGS. 8C and 8E illustrate an exemplary embodiment of the results of low-pass filtering sphygmus waves sensed respectively by different sensors, in the filtering unit, according to the invention.
Figure 8D:
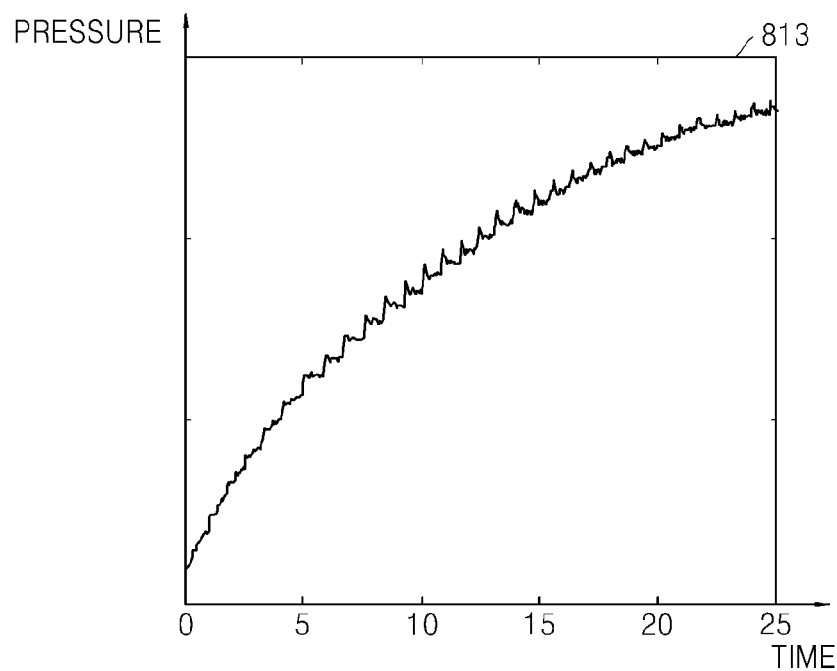

FIGS. 8B and 8D illustrate an exemplary embodiment of sphygmus waves sensed respectively by different sensors of the sensing unit 12, according to the invention. Referring to FIGS. 8B and 8D, reference numeral 811 denotes a sphygmus wave sensed at the local skin surface nearest to the radial artery, and reference numeral 813 denotes a sphygmus wave sensed at a local skin surface far away from the radial artery.

Figure 8E:
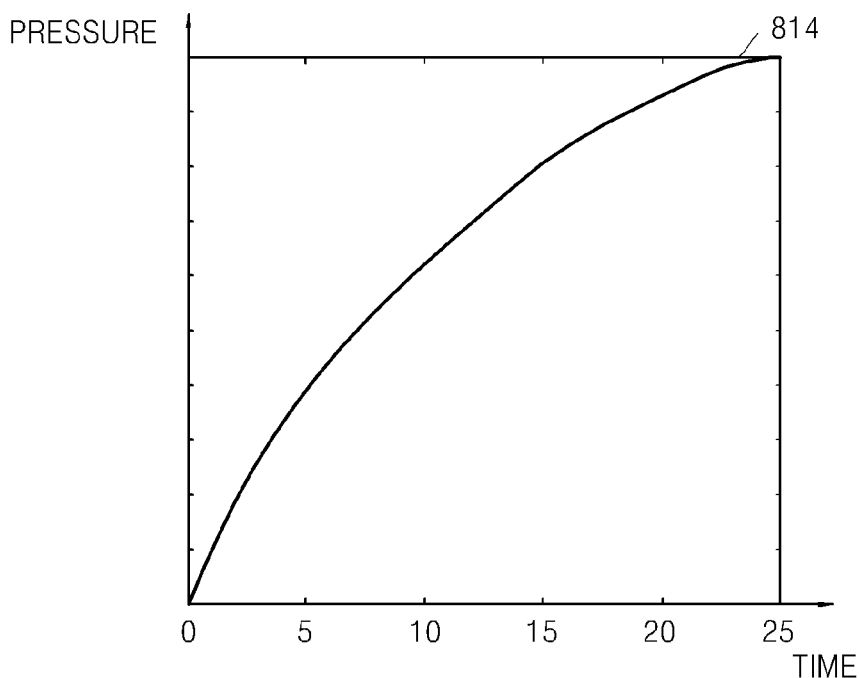

FIGS. 8C and 8E illustrate an exemplary embodiment of the results of low-pass filtering the sphygmus waves sensed respectively by different sensors, in the filtering unit 1311, according to an embodiment of the invention. Low-pass filtering the sensed sphygmus waves may be performed using a general finite impulse response ("FIR") filter, infinite impulse response ("IIR"), or a general LPF. However, when using a general LPF, a distortion or a temporal delay may occur in filtered waveforms, and thus the following method may further be used.

Referring to FIGS. 8C and 8E, reference numeral 812 denotes the results of filtering the sphygmus wave sensed at the local skin surface nearest to the radial artery, through the LPF. Reference numeral 814 denotes the results of filtering the sphygmus wave sensed at another local skin surface far away from the radial artery, through the LPF. In other words, reference numeral 812 denotes an envelope obtained from the sphygmus wave 811 (FIG. 8B), and reference numeral 814 denotes an envelope obtained from the sphygmus wave 813 (FIG. 8D).

When obtaining the envelope 812 from the sphygmus wave 811, peaks 815 and valleys 816 (FIG. 8B) of the sphygmus wave 811 sensed at the local skin surface nearest to the radial artery are used. A peak envelope is obtained by interpolating the peaks 815 (for example, using a $7^{th}$-order polynomial curve fitting method), and a valley envelope is obtained by interpolating the valleys 816. The pressure in the radial artery corresponds to a value between the peak envelope value and the valley envelope value. Thus, the envelope corresponding to the pressure in the radial artery may be obtained using Equation 1 below.

$$P = \alpha \cdot (\text{peak envelope value}) + \beta \cdot (\text{valley envelope value}) \quad \text{[Equation 1]}$$

In Equation 1, P denotes the pressure in the radial artery, and $\alpha$ and $\beta$ are values previously calibrated using invasively measured blood pressure or values derived from coefficients that determine the mean value of the sphygmus wave. In Equation 1, the peak envelope value and the valley envelope value are obtained at the same point of time. In other words, an envelope corresponding to changes in the pressure P in the radial artery may be obtained using Equation 1.

A peak envelope and a valley envelope of the sphygmus wave 811 are obtained, and the envelope 812 (FIG. 8C) is obtained using the peak envelope, the valley envelope and Equation 1. In addition, a peak envelope and a valley envelope of the sphygmus wave 813 sensed at a local skin surface far away from the radial artery are obtained, and the envelope 814 is obtained using the peak envelope, the valley envelope and Equation 1. Since the envelope 812 is obtained using the sphygmus wave sensed at the local skin surface just overlying the radial artery, characteristics of the radial artery being deformed by the pressure are well reflected in the envelope 812.

However, since the envelope 814 is obtained using the sphygmus wave sensed at the local skin surface away from the radial artery, the pressure has a monotonically increasing pattern, as illustrated in FIG. 8E. Unlike the envelope 814, which monotonically increases, the slope of the envelope 812 suddenly decreases and sharply increases again (e.g., inflects), as illustrated in FIG. 8C. The reason that the envelope 812 has an inflecting pattern lies in the characteristic that the radial artery expands and relaxes due to the compliance of the radial artery. Thus, the compliance of the radial artery gradually decreases as the radial artery is deformed with an increasing pressure applied to pressurize the radial artery, and then gradually increases when a threshold value of deformation is equal to or greater than a reference amount. Which of the plurality of sensors has sensed the sphygmus wave at the local skin surface nearest to the radial artery may be determined using the sphygmus waves filtered through the LPF.

An exemplary embodiment of a method of determining whether a sphygmus wave has been sensed at the local skin surface nearest to the radial artery by using the sphygmus waves filtered through the LPF is as follows. Herein, slopes of the envelope of the pressures in the radial artery at arbitrary points of time are calculated for the determination whether a sphygmus wave has been sensed at the local skin surface nearest to the radial artery. The envelope of the pressures in the radial artery is obtained using the sphygmus waves filtered through the LPF. In other words, slopes S1, S2, S3 and S4 of the envelope 812 (FIG. 8C), which is obtained using the sphygmus wave 811, are calculated at points of time t1, t2, t3 and t4, respectively. In contrast, the slope of the envelope 814 gradually decreases with time, but never increases.

With regard to the envelope 812, the slope decreases from S1 to S2 as the time passes from t1 to t2, increases from S2 to S3 as the time passes from t2 to t3, and gradually decreases from S3 to S4 as the time passes from t3 to t4. Thus, the minimum slopes of the envelopes of the sphygmus waves in an inflection zone where the slope that has decreased starts to increase are compared, or the maximum slopes of the envelopes of the sphygmus waves in an inflection zone where the slope that has increased starts to decrease are compared, to select the envelope having the smallest minimum slope or the envelope having the largest maximum slope as the envelope on which the pressures in the radial artery are well reflected. Thus, the envelope having the smallest minimum slope or the largest maximum slope is the envelope of the sphygmus wave sensed at the local skin surface nearest to the radial artery.

Alternatively, assuming that the envelopes of the sphygmus waves have a minimum slope that decreases firstly, and a maximum slope that increases firstly following the firstly decreasing minimum slope and before the slope starts to increase secondarily, the envelope having the largest difference between the minimum slope and the maximum slope may be determined as the envelope of the sphygmus wave sensed at the local skin surface nearest to the radial artery. In other words, the user may select a method of determining which envelope is of the sphygmus wave sensed at the local skin surface nearest to the radial artery, according a usage environment. It will be understood by those of ordinary skill in the art that the method of determining which envelope is of the sphygmus wave sensed at the local skin surface nearest to the radial artery is not limited to the above methods.

Figure 11:
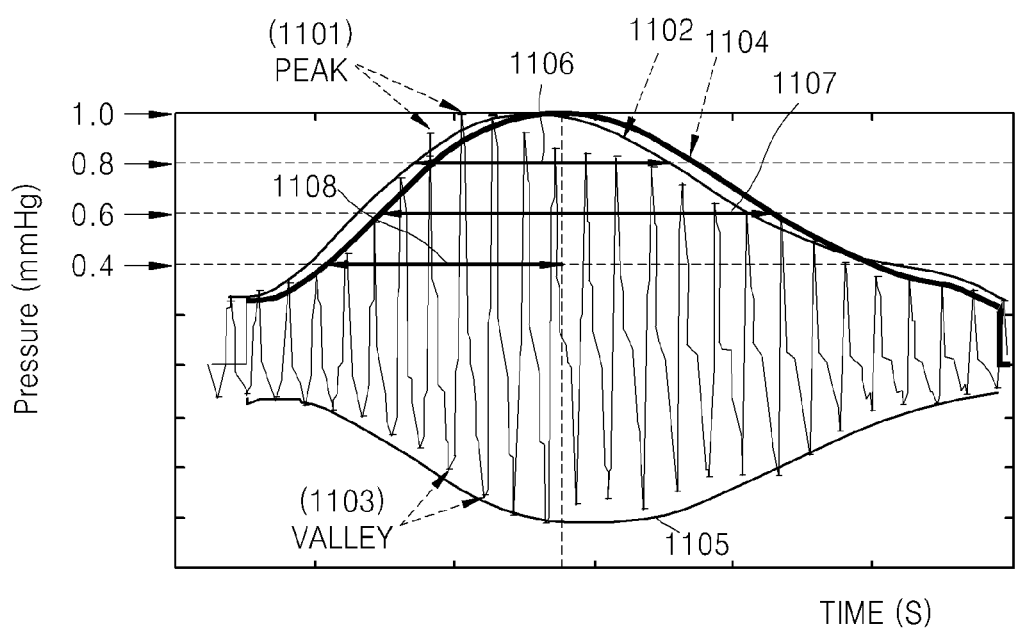
FIG. 11 illustrates an exemplary embodiment of selecting the sphygmus wave sensed at a local skin surface region nearest to the radial artery, by using the results of the filtering unit high-pass filtering sphygmus waves which are sensed by one sensor.

FIG. 11 illustrates an exemplary embodiment of selecting the sphygmus wave sensed at a local skin surface region nearest to the radial artery, by using the results of the filtering unit 1311 high-pass filtering sphygmus waves which are sensed by a plurality of sensors. Referring to FIG. 11, a sphygmus wave passed through the HPF is plotted as a graph of pressure with respect to time.

FIG. 11 illustrates a peak envelope 1102 obtained by curve-fitting peaks 1101 of the high-pass-filtered sphygmus wave, and a peak-valley envelope 1104 obtained by curve-fitting the peaks 1101 and valleys 1103. Herein, the peak-valley envelope 1104 is a result of subtracting a valley envelope 1105 obtained by curve-fitting the valleys 1103, from the peak envelope 1102. In order to select the sphygmus wave sensed at the local skin surface region nearest to the radial artery, from the sphygmus waves which are sensed by a plurality of sensors, a width of the peak envelope 1102 or the peak-valley envelope 1104 may be used.

To select the sphygmus wave sensed at a local skin surface region nearest to the radial artery, the peak envelope 1102 is obtained based on the result of high-pass filtering the sphygmus waves sensed by each of the plurality of sensors. Next, widths of the respective peak envelopes 1102 of the high-pass-filtered sphygmus waves having a predetermined ratio with respect to the maximum widths thereof, are compared to each other. In one exemplary embodiment, a width A denoted by reference numeral 1106 in FIG. 11, of the peak envelope 1102 having a ratio of 0.8 with respect to the maximum width of the peak envelope 1102, is compared with the width of each of the other peak envelopes of the other high-pass-filtered sphygmus waves having a ratio of 0.5 with respect to the maximum width of the corresponding peak envelope.

Similarly, the peak-valley envelope 1104 may be used to select the sphygmus wave sensed at a local skin surface region nearest to the radial artery. Widths of the respective peak-valley envelopes 1104 of the high-pass-filtered sphygmus waves having a predetermined ratio with respect to the maximum widths thereof are compared to each other. In one exemplary embodiment, a width B denoted by reference numeral 1107 in FIG. 11, of the peak-valley envelope 1104 having a ratio of 0.6 with respect to the maximum width of the peak-valley envelope 1104, is compared with the width of each of the other peak-valley envelopes of the other high-pass-filtered sphygmus waves having a ratio of 0.6 with respect to the maximum width of the corresponding peak-valley envelope.

In an alternative exemplary embodiment of selecting the sphygmus wave sensed at a local skin surface region nearest to the radial artery, the width of a portion of an envelope divided from a remaining portion of the envelope, based on a mean arterial pressure ("MAP") may be used. In one exemplary embodiment, a width C denoted by reference numeral 1108 in FIG. 11, of the portion of the peak-valley envelope 1104 having a ratio of 0.4 with respect to the maximum width, where the portion is divided from the remaining portion based on the MAP, is compared with the width of a portion of each of the other peak-valley envelopes.

The width of the envelope obtained by curve-fitting the sphygmus wave sensed at the local skin surface region nearest to the radial artery, the width having a predetermined ratio with respect to the maximum width thereof as described above, is smallest among the widths of the envelopes from the sphygmus waves sensed at local skin surface regions. Thus, the selection unit 1313 selects one sensor of the plurality sensors that has sensed the sphygmus wave used to obtain the envelope having the smallest width, based on the results of the comparing in the comparison unit 1312.

The blood pressure estimation unit 132 (FIG. 1) estimates blood pressure based on the sphygmus wave sensed by the sensor selected by the selection unit 1313. Herein, the sphygmus wave sensed by the selected sensor is determined to be the sphygmus wave sensed at the local skin surface nearest to the radial artery. Thus, if this sphygmus wave is used to estimate blood pressure, including systolic blood pressure and diastolic blood pressure, blood pressure approximate to the actual systolic blood pressure and diastolic blood pressure of the radial artery may be measured, thereby improving accuracy in blood pressure measurement.

The blood pressure estimation unit 132 estimates blood pressure according to the volume oscillometric method using the sensed sphygmus wave and statistical characteristic ratios. However, the method used to estimate blood pressure in the blood pressure estimation unit 132 is not limited, and it will be understood by those of ordinary skill in the art that any method of estimating blood pressure using the sphygmus wave sensed by the selected sensor may be implemented in various forms.

The blood pressure estimated by the blood pressure estimation unit 132 may include systolic blood pressure and diastolic blood pressure. However, the blood pressure estimated by the blood pressure estimation unit 132 is not limited and may be determined by the user according to a usage environment, and may be, for example, to estimate a mean blood pressure. The blood pressure estimation unit 132 transmits the estimated blood pressure to the user interface unit 15 (FIG. 1).

The user interface unit 15 outputs the blood pressure estimated by the blood pressure estimation unit 132. In other words, the user interface unit 15 outputs the blood pressure estimated based on the sphygmus wave, which is sensed by the selection unit 1313, by the blood pressure estimation unit 132. In addition, the user interface unit 15 may receive information on, for example, date of use, time of use, physical information, etc.

The user interface unit 15 may include any device displaying visual information (for example, a display, a liquid crystal display ("LCD") screen, a light-emitting diode ("LED") display, a division display device, etc.), any device providing the user with auditory information (for example, speakers, etc.), etc. In addition, the user interface unit 15 may obtain information, such as physical information, etc., from the user by using any type of information input device or method, for example, a keyboard, a mouse, a touch screen, speech recognition, etc.

Referring again to FIG. 1, the storage unit 14 stores all the results obtained from processing performed by the pressurizing unit 11, the sensing unit 12, the processor 13, the user interface unit 15, the actuator 16, and the control unit 17. In addition, the pressurizing unit 11, the sensing unit 12, the processor 13, the user interface unit 15, the actuator 16, and the control unit 17 may read information stored in the storage unit 14 when required. Furthermore, since the processor 13 includes the sensor data analysis unit 131 and the blood pressure estimation unit 132, and the sensor data analysis unit 131 includes the filtering unit 1311, the comparison unit 1312 and the selection unit 131, the storage unit 1313 may store all the results obtained from processing by these units when required.

The control unit 17 controls operations of the sensing unit 12, the processor 13, the storage unit 14, the user interface unit 15, and the actuator 16.

Figure 9:
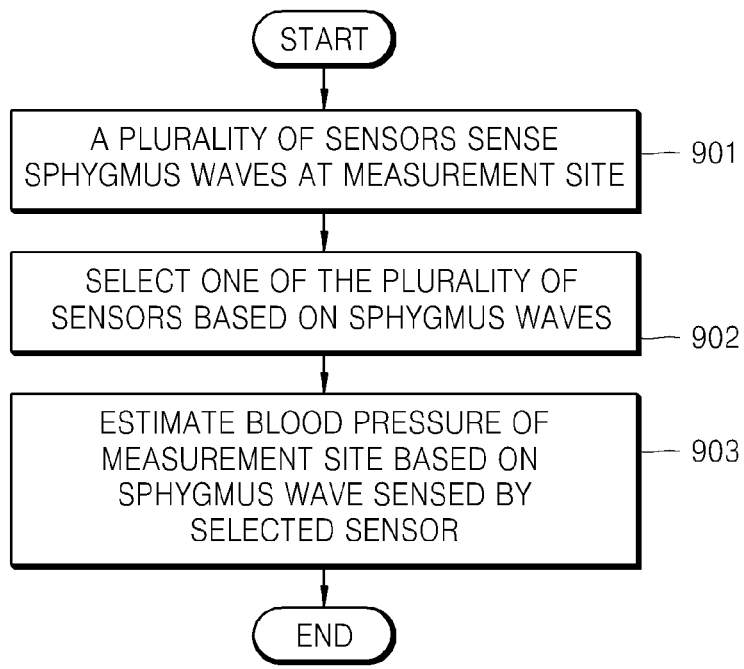
FIG. 9 is a flowchart of an exemplary embodiment of a method of measuring blood pressure, according to the invention.

FIG. 9 is a flowchart of an exemplary embodiment of a method of measuring blood pressure, according to the invention. Referring to FIG. 9, the method includes operations performed sequentially in the blood pressure measuring apparatus 1 in FIG. 1. Therefore, although not explicitly described in the illustrated embodiment, the content described above in connection with the blood pressure measuring apparatus 1 in FIG. 1 shall apply to the method of measuring blood pressure according to the illustrated embodiment.

In operation 901, each of the sensors of the sensing unit 12 senses sphygmus waves at a wrist region at which a blood pressure is to be measured.

In operation 902, the selection unit 1313 selects one of the plurality of sensors of the sensing unit 12 based on the sphygmus waves sensed by the sensors.

In operation 903, the blood pressure estimation unit 132 estimates blood pressure of the measurement site based on the sphygmus wave sensed by the selected sensor in operation 902.

Figure 10:
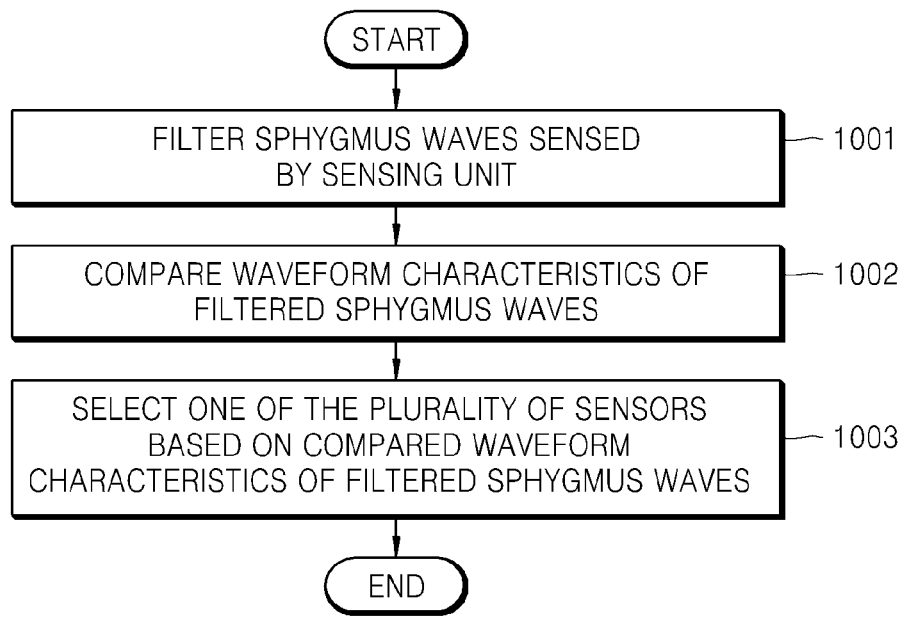
FIG. 10 is a detailed flowchart of an exemplary embodiment of an operation of selecting one of a plurality of sensors of a sensing unit based on sensed sphygmus waves in FIG. 9.

FIG. 10 is a detailed flowchart of an exemplary embodiment of operation 902 in FIG. 9. Referring to FIG. 10, operation 901 of FIG. 9 may involve operations sequentially performed in the sensor data analysis unit 131 illustrated in FIGS. 1 and 6. Therefore, although not explicitly described in the illustrated embodiment, the content described above in connection with the sensor data analysis unit 131 shall apply to the embodiment illustrated in FIG. 10.

In operation 1001, the filtering unit 1311 filters the sphygmus waves, which are sensed by the plurality of sensors of the sensing unit 12, by passing the sphygmus waves through both a HPF and a LPF.

In operation 1002, the comparison unit 1312 compares waveform characteristics of the filtered sphygmus waves. In the comparing the waveform characteristics, the comparison unit 1312 compares the maximum amplitudes of the sphygmus waves filtered by the HPF, or compares slope characteristics of the sphygmus waves filtered by the LPF.

In operation 1003, the selection unit 1313 selects one of the plurality of sensors of the sensing unit 12 based on the waveform characteristics of the filtered sphygmus waves compared by the comparison unit 1312. The selected one sensor senses the sphygmus wave at the local skin surface nearest to the radial artery.

As described above, according to the one or more of the above embodiments of the invention, a sphygmus wave that is the most approximate to an actual sphygmus wave from a blood vessel in which the blood pressure to be measured, may be found by analyzing the sphygmus waves sensed by a plurality of sensors of the sensing unit attached to the pressurizing element, and blood pressure is measured using this sphygmus wave, thereby improving accuracy in blood pressure measurement.

The embodiments of the invention may be written as computer processing programs and may be implemented in general-use digital computer processors that execute the programs using a computer readable recording medium. Data used in the above-described embodiments may be recorded on a medium by various elements. The computer readable recording medium includes magnetic storage media (e.g., read-only memory ("ROM"), floppy disks, hard disks, etc.) and/or optical recording media (e.g., compact disc read-only memory ("CD-ROMs"), or Digital Versatile/Video Disc ("DVDs")).

While this invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the invention.

What is claimed is:

1. A blood pressure measuring apparatus comprising:
a sensing unit comprising a plurality of sensors each sensing a sphygmus wave at a same measurement site;
an analysis unit which
filters each sphygmus wave,
generates an envelope for each filtered sphygmus wave, and
calculates a waveform characteristic value for each envelope from slopes or slope variations of the each envelope;
a comparison unit comparing the characteristic values of the envelopes to determine the smallest or largest characteristic value, among the characteristic values of the envelopes;
a selection unit selecting one sensor of the plurality of sensors which sensed the sphygmus wave, the envelope of which has the smallest or largest characteristic value; and
a blood pressure estimation unit estimating blood pressure of the measurement site based on the sphygmus wave which is sensed by the selected one sensor.

2. The blood pressure measuring apparatus of claim 1, wherein
the analysis unit filters the each sphygmus wave through a high-pass filter to pass a high-frequency component of the each sphygmus wave, and determines a maximum amplitude of the each filtered sphygmus wave; and
the comparison unit compares the determined maximum amplitudes of the filtered sphygmus waves to determine the largest maximum amplitude.

3. The blood pressure measuring apparatus of claim 2, wherein the selected one sensor sensed the sphygmus wave, of which the filtered sphygmus wave has the largest maximum amplitude.

4. The blood pressure measuring apparatus of claim 1, wherein the analysis unit
filters the each sphygmus wave through a low-pass filter to pass a low-frequency component of the each sphygmus wave,
generates the envelope from each low-pass filtered sphygmus wave, and
calculates the characteristic value for the each envelope from the slopes or the slope variations of the each envelope.

5. The blood pressure measuring apparatus of claim 4, wherein
the analysis unit
determines for the each envelope, an envelope inflection zone where a slope of the envelope consecutively increases and decreases, and
calculates for the each envelope, a maximum slope and a difference between the increasing slope and the decreasing slope in the envelope inflection zone, and
the comparison unit compares the maximum slopes and the differences, to determine the largest maximum slope and the largest difference, and
wherein
the selected one sensor sensed the sphygmus wave, the envelope of which has the largest maximum slope, or
the selected one sensor sensed the sphygmus wave, the envelope of which has the largest difference.

6. The blood pressure measuring apparatus of claim 4, wherein the analysis unit
determines for the each envelope, an envelope inflection zone where a slope of the envelope consecutively decrease and increases, and
calculates for the each envelope, a minimum slope and a difference between the decreasing slope and the increasing slope in the envelope inflection zone, and
the comparison unit compares the minimum slopes and the differences, to determine the smallest minimum slope and the largest difference, and
wherein
the selected one sensor sensed the sphygmus wave, the envelope of which has the smallest minimum slope, or
the selected one sensor sensed the sphygmus wave, the envelope of which has the largest difference.

7. The blood pressure measuring apparatus of claim 4, wherein the analysis unit
interpolates peaks of the each low-pass filtered sphygmus wave to generate a peak envelope,
interpolates valleys of the each low-pass filtered sphygmus wave to generate a valley envelope, and
generates the envelope of the each low-pass filtered sphygmus wave using the peak and valley envelopes.

8. The blood pressuring measuring apparatus of claim 1, wherein
the analysis unit
filters the each sphygmus wave through a high-pass filter to pass a high-frequency component of the sphygmus wave,
curve-fits peaks within each filtered sphygmus wave, to generate a peak envelope,
calculates a maximum width of each peak envelope, and
calculates the width of the each peak envelope having a predetermined ratio with respect to the maximum width; and
the comparison unit compares the widths of the each peak envelope having the predetermined ratio, such that the selected one sensor sensed the sphygmus wave, the peak envelope of which has the smallest width having the predetermined ratio.

9. The blood pressure measuring apparatus of claim 1, wherein the sensing unit comprises a sensor array in which a plurality of a rigid substrate is arrayed, each of the rigid substrates being moveable relative to neighboring rigid substrates, and each of the rigid substrates comprising at least two sensors arrayed thereon.

10. The blood pressure measuring apparatus of claim 1, wherein the sensing unit comprises a sensor array in which a plurality of a semiconductor chip is packaged on a flexible printed circuit board, each of the semiconductor chips comprising a plurality of sensors disposed thereon.

11. The blood pressure measuring apparatus of claim 1, wherein the sensing unit comprises a sensor array in which a plurality of sensors are disposed on a flexible printed circuit board.

12. The blood pressure measuring apparatus of claim 1, wherein each of the sensors has a sensing width which is equal to or smaller than a diameter of an arterial blood vessel at the measurement site.

13. The blood pressure measuring apparatus of claim 1, wherein the measurement site is a wrist region of a subject, and the sensing unit senses sphygmus waves transferred from a radial artery to local skin surfaces of the wrist region by using the plurality of sensors sensing the transferred sphygmus waves.

14. The blood pressure measuring apparatus of claim 1, wherein the blood pressure estimation unit estimates blood pressure based on the sphygmus wave sensed by the selected one sensor, according to an oscillometric method.

15. The blood pressure measuring apparatus of claim 1, further comprising a pressurizing element configured to flexibly conform to a shape of the measurement site.

16. The blood pressuring measuring apparatus of claim 1, wherein
the analysis unit
filters the each sphygmus wave through a high-pass filter to pass a high-frequency component of the sphygmus wave,
curve-fits peaks and curve-fits valleys within each filtered sphygmus wave, to form a peak envelope and a valley envelope, respectively,
generates a peak-valley envelope for the each filtered sphygmus wave by subtracting the valley envelope from the peak envelope,
calculates a maximum width of each peak-valley envelope, and
calculates the width of the each peak-valley envelope, having a predetermined ratio with respect to the maximum width; and
the comparison unit compares the widths having the predetermined ratio, such that the selected one sensor sensed the sphygmus wave, the peak-valley envelope of which has the smallest width having the predetermined ratio.

17. The blood pressuring measuring apparatus of claim 1, wherein
the analysis unit
filters the each sphygmus wave through a high-pass filter to pass a high-frequency component of the sphygmus wave,
curve-fits peaks and curve-fits valleys within each filtered sphygmus wave, to form a peak envelope and a valley envelope, respectively,
generates a peak-valley envelope for the each filtered sphygmus wave by subtracting the valley envelope from the peak envelope,
calculates a maximum width of each peak-valley envelope,
calculates the width of the each peak-valley envelope, having a predetermined ratio with respect to the maximum width, and
determines a portion of the width of the each peak-valley envelope, occurring before the mean arterial pressure of the each peak-valley envelope; and
the comparison unit compares the width portions occurring before the mean arterial pressure of the each peak-valley envelope, such that the selected one sensor sensed the sphygmus wave, the peak-valley envelope of which has the smallest width portion occurring before the mean arterial pressure of the each peak-valley envelope.

18. A blood pressure measuring method comprising:
a plurality of sensors each sensing a sphygmus wave at a same measurement site;
an analysis unit
filtering each sphygmus wave,
generating an envelope for each filtered sphygmus wave, and
calculating a waveform characteristic value for each envelope from slopes or slope variations of the each envelope;
comparing the characteristic values of the envelopes to determine the smallest or largest characteristic value, among the characteristic values of the envelopes;

selecting one sensor of the plurality of sensors which sensed the sphygmus wave, the envelope of which has the smallest or largest characteristic value; and estimating blood pressure of the measurement site based on the sphygmus wave which is sensed by the selected one sensor.

19. A computer readable recording medium storing instructions which control at least one processor to perform a method of measuring blood pressure, the method comprising:

a plurality of sensors each sensing a sphygmus wave at a same measurement site;

an analysis unit
filtering each sphygmus wave,
generating an envelope for each filtered sphygmus wave, and
calculating a waveform characteristic value for each envelope from slopes or slope variations of the each envelope;

comparing the characteristic values of the envelopes to determine the smallest or largest characteristic value, among the characteristic values of the envelope;

selecting one sensor of the plurality of sensors which sensed the sphygmus wave, the envelope of which has the smallest or largest characteristic value; and estimating blood pressure of the measurement site based on the sphygmus wave which is sensed by the selected one sensor and outputting the results of the estimating blood pressure to a user.

* * * * *